United States Patent [19]

Shoesmith

[11] Plant 4,590

[45] Sep. 2, 1980

[54] RED CHRYSANTHEMUM NAMED CHIEFTAIN

[75] Inventor: Leonard H. Shoesmith, Woking, England

[73] Assignee: Pan-American Plant Company, West Chicago, Ill.

[21] Appl. No.: 17,408

[22] Filed: Mar. 5, 1979

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A new chrysanthemum distinguished by its vivid dark red composite flowers of medium-large size which are borne in a cyme having eight to ten open blooms on a rigid and erect stem. The foliage is large and abundant and the flower color is excellent in hot weather, which makes this plant a very fine red chrysanthemum for year around flowering, and the peduncles are long enough for cutting out individual flowers for various special uses.

4 Drawing Figures

BACKGROUND OF THE NEW PLANT

This new chrysanthemum was found by me in 1974 as a seedling of unknown parentage growing among greenhouse plants being raised for breeding purposes at West Chicago, Ill., U.S.A. The growth of this plant and the vivid red color of its profusely produced flowers caused it to be selected by me for propagation and test, which was done under my direction by means of cuttings at West Chicago, Ill. Propagation of this new plant through successive generations has demonstrated that its distinctive characteristics hold true from generation to generation and appear to be firmly fixed. This new plant is now being propagated by means of cuttings for commercial marketing at West Chicago, Ill.

DESCRIPTION OF THE DRAWINGS

My new cultivar of chrysanthemum is illustrated by the accompanying two sheets of drawings, the first of which is a photographic rendition showing the inflorescence and foliage of the plant in full bloom, the photograph having been hand painted to show the true flower colors. The second sheet of the drawings is a print of a machine made copy of typical leaves of this new plant taken at several stages of maturity.

DESCRIPTION OF THE NEW PLANT

The following is a detailed description of my new chrysanthemum based upon observations of greenhouse grown plants made at West Chicago, Ill., in 1978. The color designations are according to The R.H.S. Colour Chart published by The Royal Horticultural Society of London, England.

THE PLANT

Origin: Seedling.
Parentage: Unknown.
Classification:
*Botanic.*—Chrysanthemum Morifolium.
*Commercial.*—Greenhouse spray plant.
Form: Perennial herbaceous bush.
Height: 91 to about 122 cm.
Growth: Vigorous, strong and upright.
Foliage: Quantity — abundant.
Size of leaf.—Length — about 7.62 cm. to 18.42 cm. Width — about 4.44 cm. to about 12.70 cm.

*Shape of leaf.*—Deltoid with cleft margin.
*Surface aspect.*—Canescent.
*Color.*—Upper side — 139A. Under side — 137B.
*Venation.*—Pinnate.
*Petioles.*—Length — about 1.27 to 2.54 cm.

THE BUD

Form: Globular.
Size: The size of the bud varies in both diameter and length.
Opening rate: Normal.
Color of florets:
*When phyllaries first divide.*—154B.
*When petals begin to unfurl.*—174B.
Phyllaries: Number — about 25 to 30.
*Shape.*—Lanceolate.
*Color.*—148C.
Peduncle: Erect and rigid and of various lengths along the main stem.
*Surface aspect.*—Pubescent.
*Color.*—148C.

THE FLOWER

Flowering capability: Recommended for flowering the year around.
Blooming habit: Intermittent and profuse.
Blooms:
*Type of flower.*—Composite.
*Size.*—Medium large. Diameter — about 8 to 10 cm. Depth — about 5 to 8 cm.
*Borne.*—In a cyme.
*Shape.*—When bloom first opens, cup-shaped; becoming flat when the bloom matures.
*Florets.*—Number: both ray and disc florets are numerous. Arrangement: Imbricated. Form: Elliptic with rounded apex and entire margins. Texture: Soft. Appearance: Satiny. Color: Ray florets: Upper side — 53B. Under side — 53B. Disc Florets — 162C, 154A at center.
*Phyllaries.*—20 to 30 in number.
*Peduncle.*—Strong, upright and of various lengths. Color: 148C.
*Discoloration after full bloom.*—Ray florets fade to 45B.
*Persistence.*—The florets hang on and dry.
*Fragrance.*—Typical chrysanthemum.

*Lasting quality.*—On the plant — 4 weeks. As a cut flower — 2 weeks.

REPRODUCTIVE ORGANS

Stamens:
*Number.*—5.
*Arrangement.*—Syngenesious.
*Anthers.*—Size — insignificant.
*Filaments.*—Length — insignificant.
*Pollen.*—Color — yellow.
Pistils: Number — one for each ray and disc floret.
*Styles.*—Length — insignificant.
*Color.*—Yellow.
*Stigmas.*—Color — yellow.
Ovaries: Inferior, bicarpellate.

This chrysanthemum cultivar is particularly distinguished by its large foliage and flowers and the excellent red color of the flowers in hot weather, which makes this red chrysanthemum an excellent plant for year around flowering. The ray florets are of a vivid dark red color, which is sharply contrasted by the bright yellow and green colors of the disc, and eight to ten open flowers, with peduncles of various lengths, are borne on a rigid and erect stem which enables the florist to cut out individual flowers for various special uses.

I claim:

1. A new and distinct chrysanthemum cultivar substantially as herein shown and described, characterized by its medium-large composite flowers having dark red ray florets radiating from a disc having bright yellow and green florets, by its profuse production of open blooms borne on rigid, erect stems, and by its abundant foliage of relatively large size.

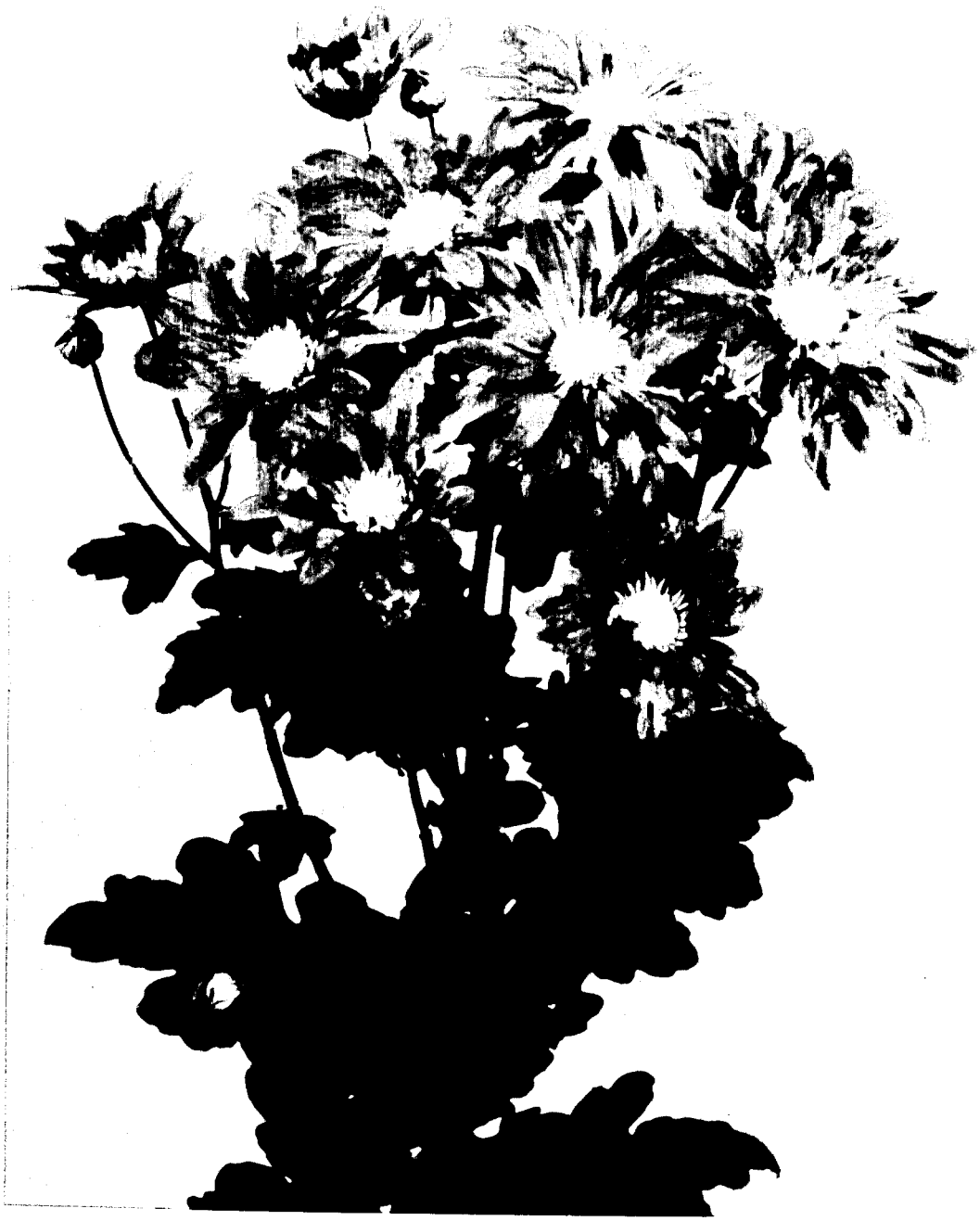

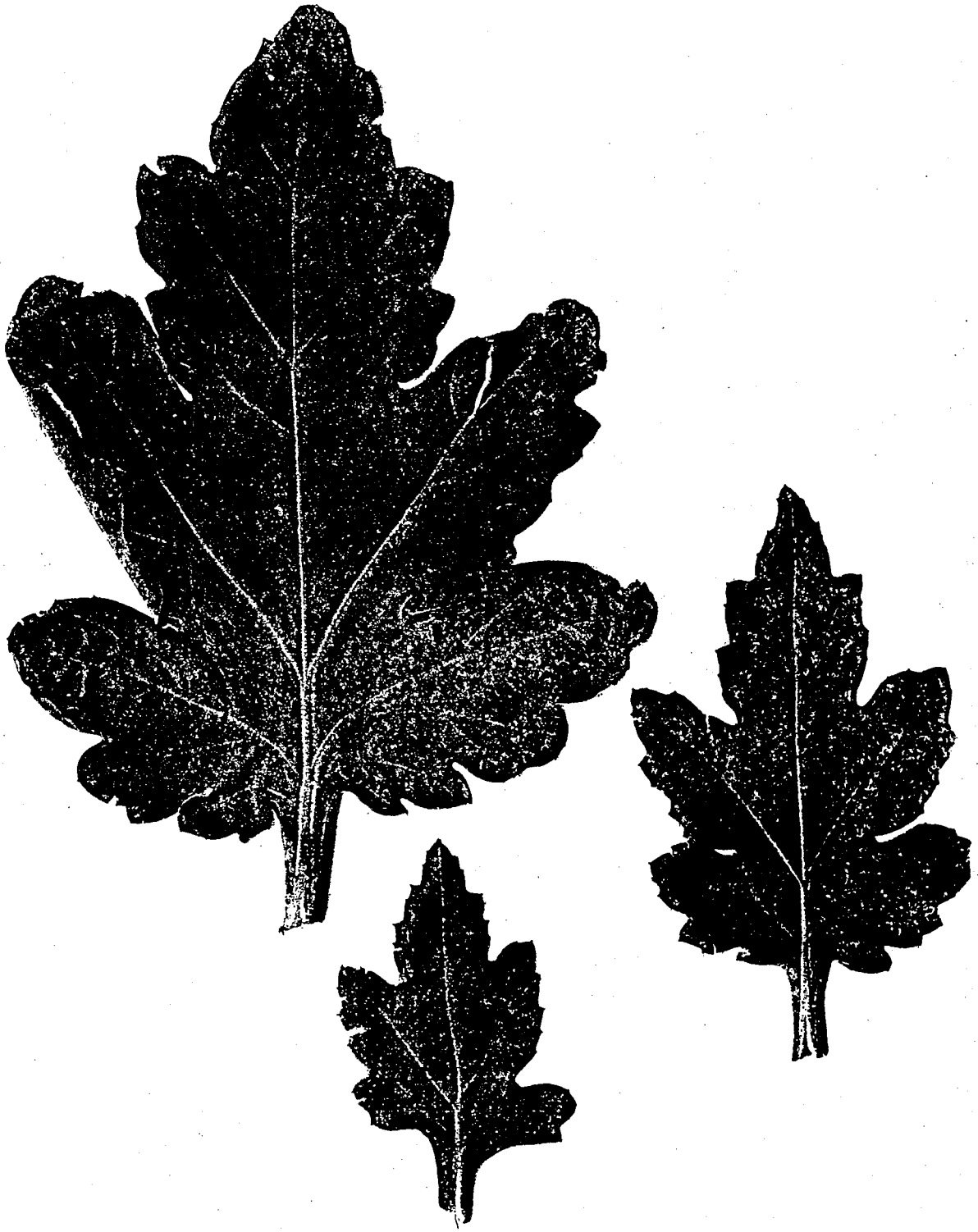

* * * * *